United States Patent
Mialhe (10) Patent No.: US 10,314,687 B2
(45) Date of Patent: Jun. 11, 2019

(54) CHIMNEY-GRAFT STENT

(71) Applicant: Claude Mialhe, Draguignan (FR)

(72) Inventor: Claude Mialhe, Draguignan (FR)

( * ) Notice: Subject to any disclaimer, the term of this patent is extended or adjusted under 35 U.S.C. 154(b) by 0 days.

(21) Appl. No.: 15/037,222

(22) PCT Filed: Nov. 4, 2014

(86) PCT No.: PCT/EP2014/073735
§ 371 (c)(1),
(2) Date: May 17, 2016

(87) PCT Pub. No.: WO2015/071135
PCT Pub. Date: May 21, 2015

(65) Prior Publication Data
US 2016/0270900 A1    Sep. 22, 2016

(30) Foreign Application Priority Data
Nov. 18, 2013 (FR) ........................ 13 61292

(51) Int. Cl.
*A61F 2/07* (2013.01)
*A61F 2/89* (2013.01)
*A61F 2/90* (2013.01)
*A61F 2/06* (2013.01)

(52) U.S. Cl.
CPC ............. *A61F 2/07* (2013.01); *A61F 2/89* (2013.01); *A61F 2/90* (2013.01); *A61F 2002/061* (2013.01); *A61F 2002/075* (2013.01); *A61F 2220/0075* (2013.01); *A61F 2230/0023* (2013.01); *A61F 2250/0039* (2013.01)

(58) Field of Classification Search
CPC ........ A61F 2/06; A61F 2/07; A61F 2002/061; A61F 2002/068; A61F 2002/065; A61F 2002/067; A61F 2002/072; A61F 2002/075
See application file for complete search history.

(56) References Cited

U.S. PATENT DOCUMENTS

| | | | |
|---|---|---|---|
| 2008/0109066 A1 | 5/2008 | Quinn | |
| 2008/0262594 A1* | 10/2008 | Morris | A61F 2/07 623/1.13 |
| 2011/0270380 A1 | 11/2011 | Bruszewski | |
| 2012/0109279 A1 | 5/2012 | Mayberry | |
| 2013/0103134 A1 | 4/2013 | Minion | |
| 2013/0172984 A1* | 7/2013 | Greenberg | A61F 2/954 623/1.24 |
| 2013/0289701 A1 | 10/2013 | Coghlan | |

FOREIGN PATENT DOCUMENTS

WO    2011/158045 A1    12/2011

OTHER PUBLICATIONS

International Search Report for corresponding International PCT application No. PCT/EP2014/073735 dated Jan. 15, 2015.

\* cited by examiner

*Primary Examiner* — Dinah Baria
(74) *Attorney, Agent, or Firm* — Hauptman Ham, LLP (57) ABSTRACT

A stent-graft suitable for chimney grafting comprising a sheath and a tubular framework defining a lumen. The stent-graft comprises, at one end of the sheath, at least one bucket formed at the end so as to form a depression in the sheath able to mate with a collateral stent. The stent-graft is applicable to the treatment of vascular pathologies, in particular to treat aneurysms. More particularly, the stent-graft is an endoprosthesis designed to be placed in parallel with at least one other endoprosthesis.

17 Claims, 4 Drawing Sheets

FIG. 14

CHIMNEY-GRAFT STENT

FIELD OF THE INVENTION

The present invention relates to a stent particularly for chimney grafting in the body of humans or animals.

The invention will find an application for the treatment of vascular diseases, notably the treatment of aneurysms. More particularly, the stent according to the invention is a stent intended to be placed in parallel with at least one further stent in the blood vessel.

STATE OF THE RELATED ART

An aneurysm is a localised dilation of the wall of a blood vessel, notably an artery, resulting in the formation of a pocket of variable size. A ruptured aneurysm represents a potentially fatal vascular accident. It is thus essential to treat the aneurysm before the vessel ruptures.

An aneurysm can be treated by open surgery and, increasingly commonly, by endovascular surgery. This technique is often preferred as it is less invasive. It consists of placing, inside the damaged area of the aorta for example, a stent to exclude the aneurysm from the blood flow. The stent is fitted without opening the aorta; it is inserted via other peripheral blood vessels.

The aneurysm may be located in an area of the artery where branches to secondary vessels are located. It is then necessary to simultaneously exclude the aneurysm from the blood flow while maintaining the blood flow in the secondary vessels.

The chimney grafting technique consists of placing a main stent in the artery to be treated and inserting collateral stents in parallel with the main stent to provide the connection between the artery and the secondary vessels for which it is sought to maintain the blood flow. The collateral stents are arranged in parallel and outside the main stent. This technique makes it possible to ensure the permeability of the blood flow in the artery via a main stent and the secondary blood flow while excluding the aneurysmal segment.

The main advantages of this chimney grafting are the simplicity of positioning and the availability of the equipment compared to other techniques particularly fenestrated grafting requiring custom manufacture, and extremely precise positioning.

However, the main drawback is the risk of leakage between the two stents due to mechanical conflicts therebetween liable to result in an endoleak in the aneurysmal sac.

US-A1-20130203134 discloses a collateral stent for secondary vessels having a non-circular cross-section suitable for being deformed to be adapted, on one hand, to the main stent, and, on the other, to the artery, so as to limit endoleaks between the parallel stents. This technique is not satisfactory as the deformation of collateral stent is relatively difficult to control and relatively instable. The blood flow in the second vessel is not sufficient.

Therefore, there is a need for a stent that is suitable for both treating the aneurysm while enhancing the connections with the secondary vessels.

SUMMARY OF THE INVENTION

For this purpose, the present invention relates to a stent comprising in one of the end portions thereof, preferentially in the proximal portion, at least one godet oriented towards said, preferentially proximal, end of the stent forming a depression in the periphery of the stent suitable for mating with a collateral stent.

The presence of the godet in the proximal portion makes it possible to form, in the main stent, a space for the collateral stent while optimising the mating between the two stents. The collateral stent does not deform, or to a slight degree, the main stent which retains a substantially circular cross-section whereas the collateral stent is also oriented in the prolongation of the connection with the secondary vessel without deformation or slight deformation.

Preferably, the stent comprises a plurality of godets on the periphery of the stent so as to facilitate the positioning of the stent without requiring precise adjustment, notably angular, for the insertion of the collateral stent.

Further aims and advantages will emerge in the course of the following description of a preferred embodiment.

It should be noted that the present invention relates to a stent suitable for chimney grafting comprising a tubular sheath and a tubular framework defining an aperture characterised in that the stent comprises, at one end of the sheath, at least one godet formed towards said end so as to form a depression in the aperture, the depression being intended to mate with a collateral stent.

According to preferred, but non-limiting, alternative embodiments of the invention, the stent is such that:
- the godet is formed by the sheath;
- at the godet, the framework is configured to leave the godet free in terms of deformation;
- the sheath at least partially covers the framework;
- the sheath and the framework are overlaid;
- the sheath is shorter than the framework;
- the framework comprises at the proximal end of the sheath a peripheral metal wire arranged in a "z" shape and comprising proximal vertices towards the proximal end, the at least one godet being formed between two successive proximal vertices;
- the godet is held by default in a folded position in the form of a pleat;
- the pleat is held by removable attachment means;
- the attachment means are arranged on the outer face of the sheath;
- the pleat formed comprises a main component oriented along the longitudinal axis of the stent;
- the pleat aligns the godet on the periphery of the framework;
- the stent comprises a plurality of godets on the periphery of the sheath;
- the godets are formed between the proximal vertices of the peripheral metal wire of the framework arranged in a "z" shape.

According to a further aspect, the invention relates to a stent system suitable for chimney grafting comprising a main stent and a collateral stent intended to be assembled in parallel in a human or animal blood vessel characterised in that the main stent comprises, at one end, at least one godet formed towards said end so as to form a depression receiving the collateral stent on a portion of the outer surface of the main stent.

According to a further separable aspect of the invention, the godet has a maximum depth equal to the diameter of the collateral stent, preferentially half the diameter.

Advantageously, the stent suitable for chimney grafting comprises a tubular framework associated with a tubular sheath, the stent being configured to adopt a compressed position and a deployed position characterised in that the sheath and the framework are in contact at one end of the sheath respectively at the level of at least two contact points on the sheath and at least two bearing points on the framework in the deployed position, the length of the sheath between the two contact points of said sheath being greater than the distance between the two bearing points of the framework so as to form a depression in the stent suitable for receiving a collateral stent.

According to a further aspect, the invention relates to a method for fitting a stent as described above and preferentially at least one collateral stent. The method comprises the following successive steps:

inserting the main stent in compressed form into the aorta to be treated;
deploying the main stent;
inserting a collateral stent into a secondary vessel leading to the main stent;
positioning the collateral stent partially in the secondary vessel and partially in parallel with the main stent in the artery at the level of a godet of the main stent;
deploying the collateral stent.

Advantageously, the collateral stent is adjoined to the outer surface of the main stent.

Advantageously, deploying the collateral stent causes the pleat to deploy.

Advantageously, the means for securing the pleat are disabled by the deployment of the collateral stent.

BRIEF DESCRIPTION OF THE FIGURES

The figures are given by way of example to illustrate and better understand the invention without being in any way restrictive.

DETAILED DESCRIPTION OF THE INVENTION

The present invention relates to a stent also known as an endoprosthesis.

The terms proximal and distal are interpreted with respect to the heart, proximal being closer to the heart and distal being more distant.

The term stent refers to a device for insertion or implantation in a part of the body of a human or animal. The stent according to the invention is intended to be inserted or implanted in the vascular system of the body of a human or animal. A stent is intended to hold the vessel wall and ensure the integrity of the diameter of the aperture thereof as much as possible. The stent is advantageously biocompatible; it can be permanent or bioabsorbable.

The stent 1 comprises a proximal end 8, a distal end 9 (both defining an opening) and an aperture 19 extending along the stent 1 to allow blood to pass from one end to the other, in the case of an artery illustrated from the proximal end 8 to the distal end 9.

The stent 1 comprises a sheath 2 also known as prosthetic tissue. The sheath 2 is a layer of material. This sheath 2 is made of leaktight material so as to restore the blood flow through the aperture 19 of the stent 1. The sheath 2 has a tubular shape. By way of example, the sheath 2 is made of Gore-Tex® or Dacron®.

The stent 1 preferentially comprises a framework 3 to hold the shape of the sheath 2. The framework 3 may be internal and/or external with respect to the sheath 2 or internal on one part and external on another. The framework 3 is, according to a first option, entirely associated with the sheath 2 or, according to a second option, the framework 3 has a part which is not associated with the sheath 2; the framework 3 is partially associated with the sheath 2, particularly being longer than the sheath. For example, the proximal portion of the framework 3 is free from the sheath 2, i.e. it is not in contact with a part of the sheath, to facilitate the securing of the stent 1 in the blood vessel; in this case, the sheath 2 is shorter than the framework 3. The framework 3 makes it possible to give the stent 1 a shape and ensure satisfactory leak-tightness with the vessel wherein the stent 1 is placed. The framework 3 makes it possible to apply the stent 1 against the walls of the vessel.

The framework 3 preferably has a tubular shape. In the present invention, the term tubular means that the structure in question defines a central channel opening of two ends via openings. Geometrically, the tubular shape may be of any elongated shape, notably cylindrical optionally with a circular cross-section. The tubular shape may optionally comprise a curve along the longitudinal direction thereof, oriented along the length of the vessel to be fitted.

The framework 3 is perforated, preferentially, the framework 3 does not interfere with secondary vessel branching zones. The framework 3 advantageously forms a mesh. A mesh pattern conventionally used is for example a Z-shaped stent. Hereinafter in the description, the term stent will be used. The framework 3 advantageously comprises at least one circular stent forming a zigzag or Z. The zigzag-shaped stent comprises a series of straight or transverse segments 7 interconnected by a series of curved segments or bends. The curved segments may comprise acute angles or vertices 6. In the Z shape, the straight segments 7 are arranged in angles, i.e. not parallel with one another and connected via vertices 6. The framework 3 is conventionally metallic, for example made of a material such as Nitinol® or cobalt-chrome; it may also be made of biocompatible and biodegradable material, for example lactic acid polymer.

The stent 1, and as such the framework 3 and the sheath 2, is flexible to adapt to the morphology of the blood vessels.

The stent 1 is configured to be compressed when fitted and subsequently expanded to fulfil the role thereof of securing the vessel and the blood flow. The stent 1 may be balloon-expandable, i.e. a balloon is inflated in the aperture 19 of the stent 1 to deploy the framework 3 which thus remains in position once the balloon has been removed and/or self-expanding, i.e. the stent 1 is deployed alone, by design once a compression stress is lifted, for example by removing an insertion tube wherein the stent is initially housed.

The stent 1 according to the invention may be used fitted on its own in the main vessel or in association with other types of stents known on the market.

The stent 1 according to the invention is intended to be positioned in blood vessels presenting with an aneurysms and branches to secondary blood vessels. Typically, the stent 1 is intended to be fitted on the renal artery or the arch of the abdominal aorta.

The stent 1 according to the invention is intended to be fitted in the main vessel, preferentially carrying the condition to be treated. At least one further stent 10 is fitted in the secondary vessel. This stent 10 is also known as an endoprosthesis. For the present description, this stent 10 is referred to as a collateral stent 10. The collateral stent 10 has a similar structure to the stent 1 as described above with a sheath 2 and a framework 3 apart from the godet 4 described hereinafter.

The stent 1 according to the invention comprises, characteristically, in a, preferentially proximal, part, a godet 4 towards said end, preferentially proximal 8, of the stent 1 forming a depression in the periphery of the prosthesis 1. The godet 4 is intended to mate with a collateral stent 10.

The godet 4 extends in the manner of a flared undulation. The godet 4 is advantageously formed in the layer of the sheath 2. The sheath 2 comprises in the proximal part thereof an undulation towards the aperture 19 of the stent 1 with flaring towards the proximal end 8.

The godet 4 is formed by an extra length of the perimeter of the sheath 2. According to one embodiment, the extra length is effective along a predefined height 16 of the sheath 2. The extra length may be fixed along the entire height 16, thus forming a sleeve. Preferentially, the extra length is increasing, optionally linearly, along this height 16 towards the proximal end of the sheath 2. Local flaring is formed therein. The flaring profile of the godet 4 may be varied. The increase may be continuous or in steps or indeed be non-existent at least along a part of the height 16.

The height 16 is chosen according to the degree of verticalisation sought for the collateral stent 10 and on the span in height required according to the number of secondary vessels to be preserved.

The godet 4 is advantageously free in terms of deformation. The framework 3 is configured to adapt for the godet 4. For example, the framework 3 follows the shape of the godet 4 in the aperture 19 of the stent. Preferentially, the framework 3 does not interfere with the godet 4. The latter may thus be in an area of the stent where the framework 3 is not present.

Figure 14:
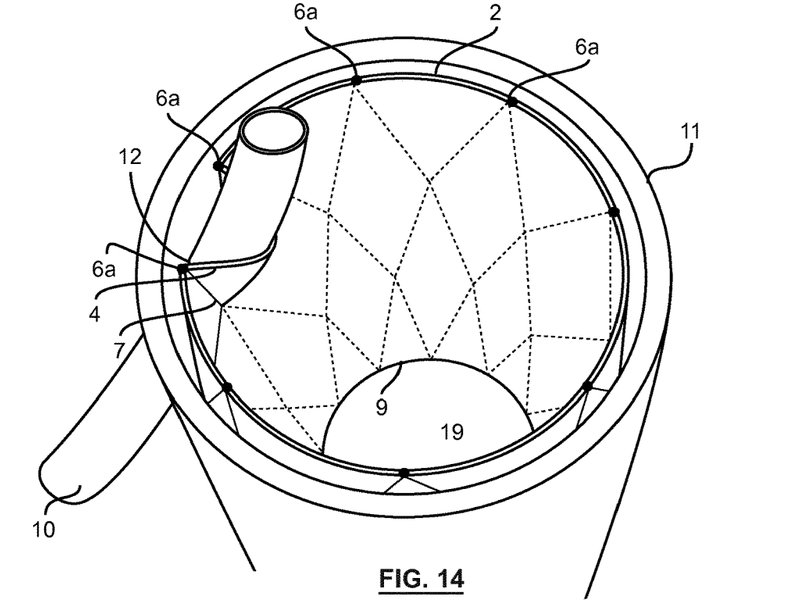
FIG. 14: perspective view of a stent according to the invention in position in an artery with a collateral stent fitted in parallel.

Advantageously, the stent 1 is applied to the inner wall of the vessel 10 at the base of the godet 4 limiting the risks of leakage from/to the aneurysmal sac. Preferentially, the stent 1 is applied mainly against the inner wall of the vessel on either side of the godet 4 as illustrated in FIG. 14. According to one option, the framework 3 contributes to this contact between the stent 1 on the periphery of the godet 4 and the inner wall of the vessel 10.

According to one preferred option, the stent 1 comprises a zigzag stent at the proximal end of the sheath 2. The godet 4 is advantageously formed between two successive proximal vertices 6a. The godet 4 then extends from a distal vertex 6b, between two successive crosspieces 7 and at most to two proximal vertices 6a. It can thus have a "V"-shaped contour along the framework 3.

According to one advantageous embodiment, the stent 1 comprises a plurality of godets 4, advantageously distributed on the periphery of the sheath 2. Various configurations are represented in FIGS. 3 to 6. Preferentially, a godet 4 is formed between each proximal vertex 6a of the Z-shaped stent at the proximal end of the sheath 2. The presence of a plurality of godets 4 makes it possible to fit a plurality of stents in parallel and thus maintain the blood flow in a plurality of secondary blood vessels 12.

The presence of godets 4 along the periphery of the sheath 2 or along a plurality of angular sectors is thus particularly advantageous as this arrangement makes it possible to easily position the stent 1 and at least one collateral stent 10 without needing to orient the stent 1 facing the opening of the branches of the secondary vessels 12. This enables the surgeon to save substantial time during the surgical procedure.

Preferably, the godet 4 is held by default in a folded position for example by removable attachment means 14. The term attachment means denotes an attachment element. The godet 4 is suitable for successively adopting a folded position and deployed position wherein it is intended to mate with a collateral stent 10. Advantageously, in the folded position, the godet 4 forms a pleat 15. The term pleat 15 denotes that the sheath 2 is folded back onto itself to form a double thickness. The pleat 15 is advantageously held by removable attachment means 14. In the folded position, the godet 4 is situated in the periphery of the sheath 2. The godet 4 is aligned in the diameter of the stent 1. It follows the profile of the framework 3. The godet 4 does not form a depression in the aperture 19 of the stent 1. The blood flow cannot be impeded. The folded position of the godet 4 is secured when the godet 4 does not mate with a collateral stent 10. The pleat 15 is also advantageously secured during the fitting of the stent. Once a collateral stent 10 is fitted, the pleat 15 is unfolded and the godet 4 is in the deployed position so as to receive the collateral stent 10. The collateral stent 10 is applied on the outer fact of the stent 1 and more particularly of the sheath 2 at the godet 4.

The attachment means 14 are removable to enable the release of the godet 4. For example, by inflating a balloon when fitting the collateral stent 10.

The removable attachment means 14 are chosen notably from staples to be untwisted, anchors with adjoined branches, knots in a breakable yarn, polymer adhesive, lacing for example self-tightening or self-loosening. By way of example, 8/0 or 10/0 yarn is satisfactory. Preferentially, the removable attachment means 14 are arranged on the outer face of the sheath 2. In this way, when the godet 4 is deployed, the attachment means 14 are retained on the outer face of the sheath 2 and are not liable to be carried into the blood flow.

This folded position of the godet 4 is particularly advantageous when the stent 1 comprises a plurality of godets 4. As such, the unused godets 4 are held in the folded position and do not interfere in the aperture 19 of the prosthesis 1.

By way of preferred example, the stent 1 has a deployed diameter of 24 to 38 mm whereas the collateral stents 10 have diameters of 5 to 9 mm. A godet 4 in the deployed position represents 5 to 20% of the diameter of said stent 1.

Figure 1:
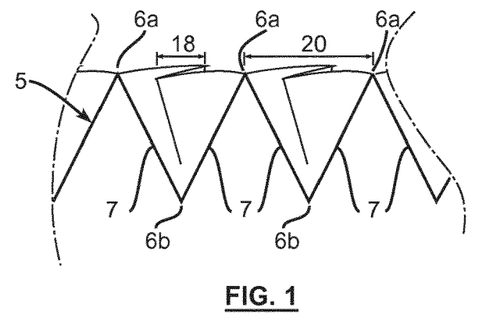
FIGS. 1 and 2: longitudinal sectional views of the proximal portion of the stent comprising a plurality of godets in the folded position (FIG. 1) and in the deployed position (FIG. 2).
Figure 2:
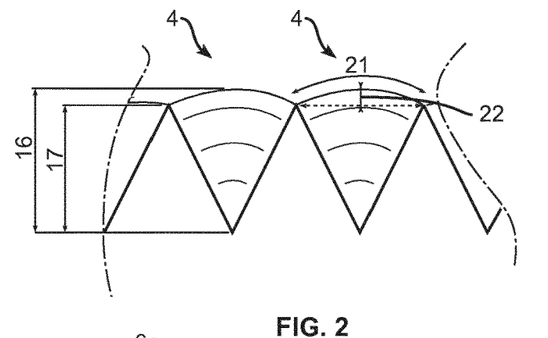
Figure 3:
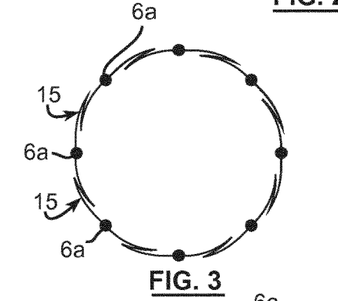
FIGS. 3 to 6: cross-sectional views of the stent, illustrating a plurality of embodiments for positioning the godets represented in the folded position except in FIG. 6 wherein a godet is in the deployed position.
Figure 4:
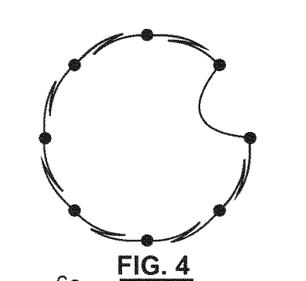
Figure 5:
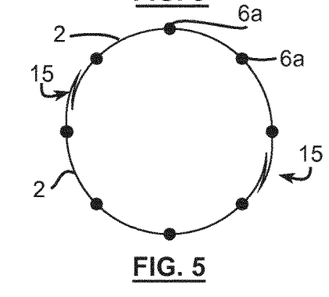
Figure 6:
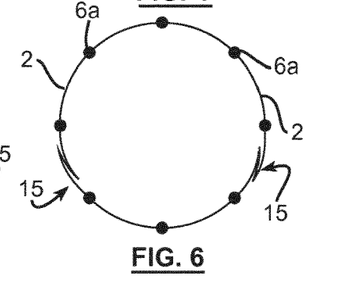

The godet 4 is configured to mate with a collateral stent 10. With reference to FIGS. 1 and 2, indicative examples of a godet 4 and pleat 15 are described hereinafter.

The godet 4 has therein a length 21 corresponding to the length of the sheath 2 between the two successive proximal vertices 6a between which the godet 4 is formed. The height 16 of the godet 4 corresponds to the distance, parallel with the longitudinal axis 23 of the stent 1, between the most distal point and the most proximal point of the godet 4.

According to one embodiment, the height 16 of the deployed godet 4 corresponds to the sum of the height of the zigzag stent and the depth 22 of the godet 4. The depth 22 of the godet 4 corresponds to the difference between the curvilinear length 21 of the godet 4 preferentially at the edge of the sheath 2 and the distance 20 between two successive proximal vertices 6a between which the godet 4 is formed. The depth 22 extends along a transverse direction to the longitudinal axis 23. For example, the depth 22 is chosen so as to be at least equal to half the diameter of the collateral stent 10 which will mate with the godet 4. The depth 22 of the godet corresponds to the depression formed in the aperture 19 of the stent 1. The height 16 of the godet 4 is suitable for enabling the parallel positioning of the collateral stent 10 from the branch with the secondary vessel 12. The godet 4 extends advantageously from the branch with the secondary vessel 12 to the end, preferentially proximal, of the sheath 2.

By way of example,
height 17 of the zigzag stent=distance CD=16 mm;
distance 20 between proximal vertices=distance A'B'=distance A'B'=15 mm;
depth 22 of the godet 4=distance C'D'=3 mm;
length 21 of the godet 4=distance A'C'+C'B'=18 mm;
height 16 of the godet 4=distance CD+D'C'=19 mm.

Figure 7:
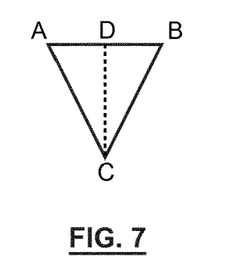
FIGS. 7 to 9: diagrams for the embodiment of the godet according to the invention.
Figure 8:
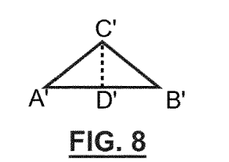
Figure 9:
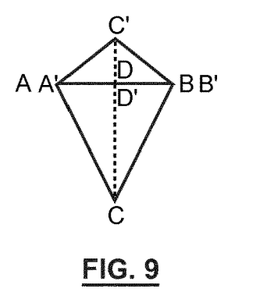
Figure 10:
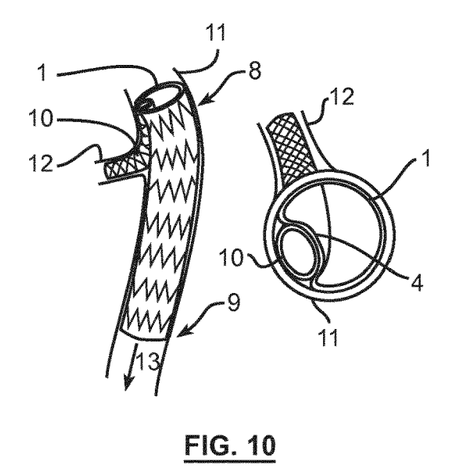
FIG. 10: principle diagram of the positioning of a chimney graft with the stent according to the invention placed in a renal artery with a cross-sectional view of the mating of the two parallel stents.
Figure 11:
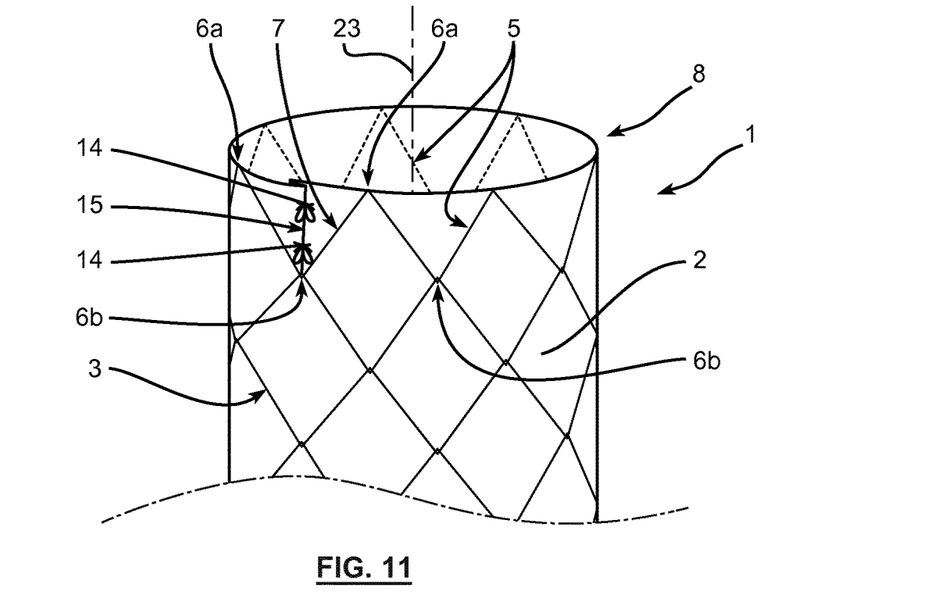
FIGS. 11 and 12: perspective views of a prosthesis according to the invention comprising a godet in the folded position (FIG. 11) in the form of a pleat secured by two removable attachment means and in the unfolded position (FIG. 12).
Figure 12:
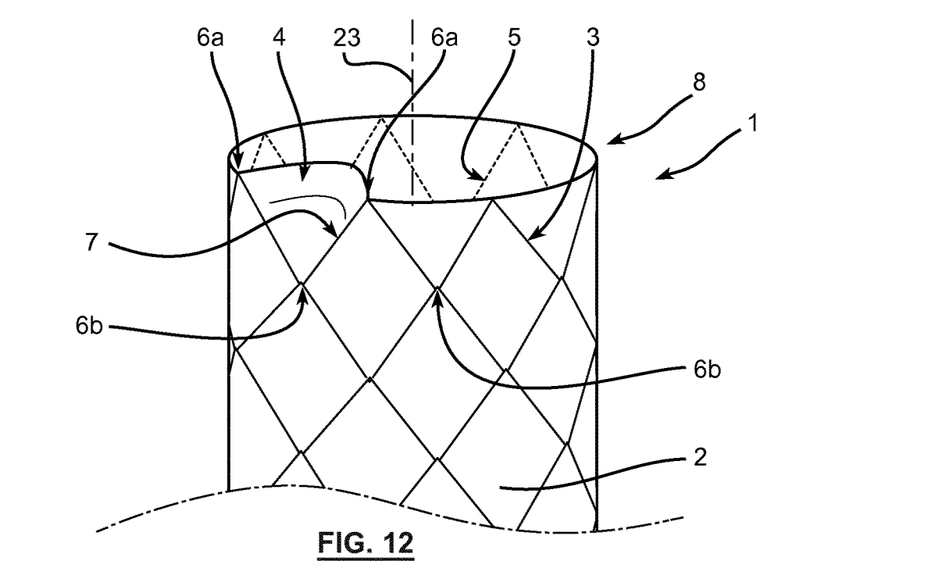

To implement a godet 4 according to the invention, it is notably possible to schematise the godet 4 as illustrated in FIGS. 7 to 9. The godet is schematised by a triangle ABC, FIG. 7, corresponding to a triangle of the Z-shaped stent where the godet 4 is formed, and a triangle A'B'C', FIG. 8. The bases AB and A'B' of the two triangles being adjoined to form the godet 4, FIG. 9.

The distance 20 between the proximal vertices corresponds to the distances AB and A'B'=15 mm. The heights of the two triangles between D'C and D'C'. D'C', corresponding to the depth 22 of the godet 4, is chosen to be equal to 3 mm corresponding substantially to half the diameter of the collateral stent 10.

It is possible to calculate on the basis of a right-angled triangle A'D'C':

$$A'C'^2 = A'D'^2 + D'C'^2$$

$$A'C'^2 = 7.5^2 + 3^2$$

$$A'C' = \sqrt{7.5} + \sqrt{3}$$

$$A'C' = 8.87$$

The distance A'C' may be rounded to 9 mm, i.e. a distance A'C'+C'B' of 18 mm corresponding to the length 21 of the godet 4.

In the folded position, advantageously the default position, the godet 4 is in the form of a pleat 15. The height 18 of the pleat 15 corresponds to the length of the part of the sheath 2 folded back onto itself to form the pleat. Advantageously, the height 18 of the pleat is equal to the depth 22 of the godet 4. Indeed, the depth 22 of the godet 4 is the extra length of the sheath 2 with respect to the distance 21 between the two proximal vertices 6a. It is this extra length that needs to be folded back so that the sheath 2 is positioned along the periphery of the stent 1 and does not form a depression in the aperture 19. When the godet 4 is in the folded position, the length 21 of the sheath 2 between two successive proximal vertices 6a is equal to the distance 20 between said two vertices 6a. The sheath 2 does not constrain the distance between the two vertices.

According to one option illustrated in all the figures, the proximal end of the sheath 2 coincides with the proximal end of the framework 3 and thus forms the proximal end of the stent 1.

According to a further option, the framework 3 is extended beyond the proximal end of the sheath 2. The proximal end of the sheath 2 is arranged at contact points on the framework 3. For the description, the contact points correspond to the proximal vertices 6a of the framework 3.

The stent 1 is configured to adopt a compressed position which is used for the positioning thereof and a deployed position wherein it is either in position in a blood vessel bearing on the inner walls of the vessel, or deployed before use.

According to one separable aspect of the invention, the chimney-graft stent comprises a tubular framework 3 associated with a tubular tube, the stent being configured to adopt at least one compressed position and one deployed position. The sheath 2 and the framework 3 are in contact at the, preferentially proximal, end of the sheath 2 at two contact points and two bearing points on the framework 3. In the deployed position, the distance 21 between the two contact points of said sheath 2 is greater than the distance 20 between the two bearing points of the framework 3. This difference in length creates a depression in the sheath 2 intended to mate with a collateral stent 10. Preferentially, this difference in length is maintained on a part of the height of the stent 1. According to one option, this difference in length is increasing along the height of the stent 1 towards the proximal end 8 of the stent 1. A godet 4 is formed therein towards the proximal end 8 of the stent 1.

According to the invention, the stent 1 is inserted into the artery to be treated in a known manner by compressing the stent 1. Once the stent 1 is placed in the area of the artery 11 to be treated, the stent 1 is deployed, either using a balloon or automatically on removing the compression stress. The blood flow is restored via the aperture 19. The positioning of the stent 1 is only checked so that the area to be treated, i.e. the aneurysm, is covered and that the stent 1 extends sufficiently on either side to maintain satisfactory leak-tightness. It is not necessary with the stent 1 according to the invention to check the radial positioning of the stent 1 facing the openings of branches of secondary vessels 12. A collateral stent 10 is inserted into a secondary vessel 12 opening at the stent 1. The collateral stent 10 is inserted in a known manner in compressed form. The collateral stent 10 is positioned partially in the secondary vessel 12 and partially in parallel with the stent 1 in the artery 11. Preferentially, the collateral stent 10 is arranged outside the stent 1.0 The longitudinal positioning of the collateral stent 10 is such that said stent 10 opens into the artery 11 at least at the proximal end 8 of the stent 1 or after said end 8. The collateral stent 10 is advantageously positioned in parallel with the stent 1 at a godet 4, which may be in the folded position in the form of a pleat 15. The collateral stent 10 is deployed by a balloon and/or automatically on removing the compression stress. The blood flow is restored via the collateral stent 10. The deployment of the collateral stent 10 gives rise to the deployment of the godet 4 with the rupture of the attachment means 14 if present. The attachment means 14 are configured to be detached from the pleat 15 by the expansion of the collateral stent 10.

In the case of a yarn, it is sufficiently fragile to be broken by the expansion force of the collateral stent. By way of example, 8/0 or 10/0 yarns have displayed satisfactory rupture. In the case of a staple or anchor, the torsional strength is chosen to be less than the expansion force of the collateral stent 10.

For polymer adhesive, the tear strength is also selected to be less than the expansion force of the collateral stent 10.

The other pleats 15 held in place by default or by attachment means 14 and which are not used for the insertion of a collateral stent 10 remain in the folded position. The expansion of the main stent 1 does not disable the attachment means 14.

The pleat 15 does not help reduce the perimeter of the stent 1. The pleat 15 does not block the expansion of the stent 1, more particularly the expansion of the framework 3.

Figure 13:
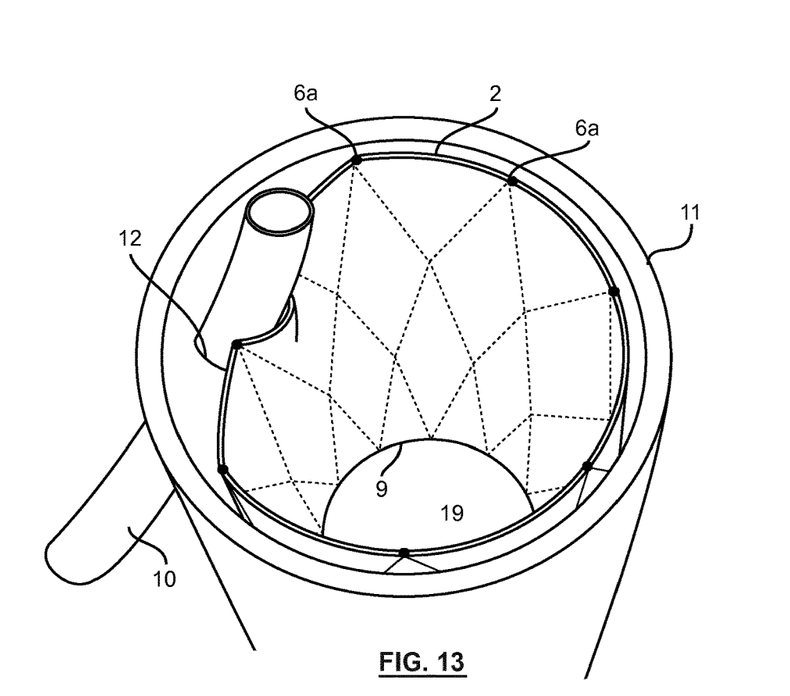
FIG. 13: perspective view of a stent according to the prior art in position in an artery with a collateral stent fitted in parallel.

In the proximal part in particular, the contact between the stent 1 and the walls of the artery 11 is maximal, the stent 1 thanks to the godet 4 is not deformed. The stent 1 holds a substantially circular shape. The stent 1 surrounds the collateral stent 10 at the godet 4 to optimise the contacts with the walls of the artery 11. FIG. 14 illustrates this arrangement which is advantageous with respect to conventional stents according to the prior art illustrated in FIG. 13 where it is possible to see the stent 1 deformed by the collateral stent preventing sufficient contact between the stent 1 and the walls of the artery 11 generating endoleaks between the two stents 1, 10.

REFERENCES

1. Stent
2. Sheath
3. Framework
4. Godet
5. Metal wire
6a. Proximal vertices
6b. Distal vertices
7. Crosspiece/straight segment
8. Proximal end
9. Distal end
10. Collateral stent
11. Artery
12. Secondary vessels
13. Blood flow
14. Attachment means
15. Pleat
16. Height of godet
17. Height of Z
18. Height of pleat
19. Aperture
20. Distance between proximal vertices
21. Length of godet
22. Depth of godet
23. Longitudinal axis of stent

The invention claimed is:

1. Stent-graft suitable for chimney grafting comprising a tubular sheath and a tubular stent framework and defining a lumen,
   wherein the stent-graft comprises, at one end of the tubular sheath, at least one godet having a folded shape at the one end, the at least one godet is configured to form a depression in the lumen in an unfolded position, the depression comprising an outer surface oriented opposite the lumen, and wherein the godet is held in the form of a pleat in a folded position,
   wherein the tubular sheath and the tubular stent framework are in contact with each other at the one end of the tubular sheath at two contact points in the unfolded position, and in the unfolded position a distance along an outer surface of the at least one godet between the two contact points of said tubular sheath is greater than a distance between the two contact points of the tubular stent framework, a difference in length between the distance along the outer surface of the at least one godet and the distance between the two contact points of the tubular stent framework is increasing along the godet toward the one end, and
   wherein the tubular stent framework comprises, at the one end of the tubular sheath comprising the godet, a peripheral metal wire arranged in a "z" shape and comprising proximal vertices toward the one end, the at least one godet being formed between two successive proximal vertices, the at least one godet extends from a distal vertex between two successive straight segments upward toward the two successive proximal vertices.

2. Stent-graft according to claim 1 wherein, the tubular stent framework is configured to leave the godet free in terms of deformation.

3. Stent-graft according to claim 1 wherein the tubular sheath at least partially covers the tubular stent framework.

4. Stent-graft according to claim 1 comprising removable attachment elements to hold the godet in the folded position.

5. Stent-graft according to claim 4 wherein the removable attachment elements are arranged on the outer surface of the godet.

6. Stent-graft according to claim 1 wherein the pleat is parallel to a longitudinal axis of the stent-graft.

7. Stent-graft according to claim 1 wherein the godet in the folded position is aligned with the periphery of the tubular stent framework.

8. Stent-graft according to claim 1 wherein an outer envelope comprising at the one end of the tubular sheath, a plurality of godets.

9. Stent-graft according to claim 8 wherein each godet of the plurality of godets being formed between two successive proximal vertices.

10. Stent-graft according to claim 1, wherein a fold line of the pleat is oriented in a direction parallel to a longitudinal axis of the stent-graft.

11. Stent-graft according to claim 1, wherein a perimeter of the tubular sheath at the one end having the at least one godet is greater than a perimeter of the tubular stent framework at the one end.

12. Stent-graft according to claim 1, wherein a length of the at least one godet in the unfolded position at the one end of the tubular sheath and between two successive proximal vertices is greater than a length of the distance between two successive proximal vertices along the at least one godet in the folded position at the one end.

13. Stent-graft according to claim 1, wherein the godet comprises an edge formed by an edge of the folded shape at the one end of the tubular sheath, the edge of the folded shape having a first end connected to a first proximal vertices and a second end connected to a second proximal vertices of the peripheral metal wire, wherein in the unfolded position a length of the folded shape edge is larger than a length of a geometrical circle arc joining first proximal vertices and second proximal vertices.

14. Stent-graft according to claim 1 wherein the godet is formed by an additional circumference along a perimeter of the tubular sheath.

15. Stent-graft system comprising a main stent and a collateral stent,
   the main stent comprising a tubular sheath and a tubular stent framework and defining a lumen wherein the stent-graft system comprises, at one end of the tubular sheath, at least one godet having a folded shape at the one end and wherein the at least one godet is configured to form a depression in the lumen in an unfolded position, the depression comprising an outer surface oriented opposite the lumen, the outer surface mating with the collateral stent, the godet is held in the form of a pleat in a folded position, and wherein the tubular sheath and the tubular stent framework are in contact with each other at the one end of the tubular sheath at two contact points in the unfolded position, and in the unfolded position a distance along an outer surface of the at least one godet between the two contact points of said tubular sheath is greater than a distance between the two contact points of the tubular stent framework, a difference in length between the distance along the outer surface of the at least one godet and the distance between the two contact points of the tubular stent framework is increasing along the godet toward the one end.

16. System according to claim 15 wherein the godet has a maximum depth equal to the diameter of the collateral stent.

17. Stent-graft suitable for chimney grafting comprising a tubular sheath and a tubular stent framework and defining a lumen, wherein the stent graft comprises, at one end of the tubular sheath, at least one godet having a folded shape at the one end, the at least one godet is configured to form a depression in the lumen in an unfolded position, the depression comprising an outer surface oriented opposite the lumen, and wherein the godet is held in the form of a pleat in a folded position, wherein the tubular sheath and the tubular stent framework are in contact with each other at the one end of the tubular sheath at two contact points in the unfolded position, and in the unfolded position a distance along an outer surface of the at least one godet between the two contact points of said tubular sheath is greater than a distance between the two contact points of the tubular stent framework, a difference in length between the distance along the outer surface of the at least one godet and the distance between the two contact points of the tubular stent framework is increasing along the godet toward the one end.

* * * * *